US011229804B1

(12) United States Patent
Walker

(10) Patent No.: US 11,229,804 B1
(45) Date of Patent: Jan. 25, 2022

(54) LIGHT THERAPY SYSTEM AND METHODS OF USING SAME

(71) Applicant: Aeth-Illume Inc., Lebanon, IN (US)

(72) Inventor: Paul R. Walker, Lebanon, IN (US)

(73) Assignee: Aeth-Illume Inc., Lebanon, IN (US)

( * ) Notice: Subject to any disclaimer, the term of this patent is extended or adjusted under 35 U.S.C. 154(b) by 0 days.

(21) Appl. No.: 17/218,270

(22) Filed: Mar. 31, 2021

Related U.S. Application Data

(60) Provisional application No. 63/005,756, filed on Apr. 6, 2020.

(51) Int. Cl.
| | |
|---|---|
| *A61N 1/40* | (2006.01) |
| *A61N 5/06* | (2006.01) |
| *A61N 1/08* | (2006.01) |
| *A61N 1/02* | (2006.01) |

(52) U.S. Cl.
CPC ............... *A61N 1/40* (2013.01); *A61N 1/025* (2013.01); *A61N 1/08* (2013.01); *A61N 5/0616* (2013.01); *A61N 2005/0652* (2013.01)

(58) Field of Classification Search
None
See application file for complete search history.

(56) References Cited

U.S. PATENT DOCUMENTS

| | | | | |
|---|---|---|---|---|
| 5,733,032 A | * | 3/1998 | Bolta | A61N 5/0618 362/217.14 |
| 5,766,233 A | * | 6/1998 | Thiberg | A61N 5/06 607/88 |
| 2007/0060984 A1 | * | 3/2007 | Webb | A61N 5/0622 607/89 |
| 2013/0289670 A1 | * | 10/2013 | Thiberg | A61N 5/0613 607/88 |
| 2014/0296945 A1 | * | 10/2014 | Kato | A61N 5/0618 607/88 |
| 2015/0231408 A1 | * | 8/2015 | Williams | A61N 5/06 607/88 |
| 2016/0158568 A1 | * | 6/2016 | Uplaznik | A61N 2/004 600/9 |

* cited by examiner

*Primary Examiner* — Michael W Kahelin
(74) *Attorney, Agent, or Firm* — Gardner, Linn, Burkhart & Ondersma LLP

(57) ABSTRACT

A light therapy system and method are provided for treating humans or terrestrial or aquatic animal and plant subjects with non-coherent light. The system includes an electrical controller configured with two supplies of voltage, high and low frequency pulse-width-modulators, adjustable high and low frequency duty cycle controllers for controlling the duty cycle outputs of the respective high and low frequency pulse-width-modulators that determine light pulsation intensities, and at least one light source electrically connected to the electrical controller and having at least two distinct light emitting elements. One light emitting element operates at high light pulsation frequencies, and another light emitting element operates at low light pulsation frequencies. The light may include a plurality of the high frequency powered light emitting elements and a plurality of the low frequency powered light emitting elements.

19 Claims, 8 Drawing Sheets

LIGHT THERAPY SYSTEM AND METHODS OF USING SAME

CROSS REFERENCE TO RELATED APPLICATION

The present application claims the benefit of U.S. provisional application Ser. No. 63/005,756, filed Apr. 6, 2020, which is hereby incorporated herein by reference in its entirety.

FIELD OF THE INVENTION

The present invention relates to a light therapy system and methods for treating terrestrial or aquatic animal and plant subjects, including human subjects.

BACKGROUND OF THE INVENTION

In the human body, water constitutes 60-70% of living body mass. A significant portion of this water is contained within the intercellular compartments and provides a lattice structure (a scaffolding, also called the hydration layer) which mediates protein folding and all cellular functions. This mediation of structural changes of proteins demands a critical level of intra-cellular energy, primarily derived from the body water in the interstitial fluid space surrounding cells. Protein misfolding, in turn, is a result of insufficient energy levels within the body water. Changes in the functional states of proteins, i.e. between active natively (normal/proper)-folded protein formations, and misfolded protein formations, are induced by energy flow, or the lack thereof, through such protein-bound water. In other words, body water either has sufficient energy, as in a charged battery, or has insufficient energy, as in a discharged battery.

Research indicates that water is susceptible to light exposure. When light comes into contact with water it induces a physical change in the structure and organization of water with formation into distinct phases of diverse physical attributes like density, pH, and ion concentration which, in turn, produce separation of electrical charges and induction of flow currents. In other words, the refractive component of incident light provides the necessary energy to effectively transform water into a battery that, in turn, can be harnessed to alter dynamics within the human body.

Up to 70-80% of chronic diseases in humans are now thought to be the result of protein misfolding, including up to 50% of cancers. Protein misfolding impairs the ability of affected proteins to perform their normal and necessary functions. While executing their functions, proteins continually undergo spatial rearrangement, alternating between related conformations as seen, for example, in contraction and dilation of heart muscle. Such changes represent transitions between discrete energy states.

The folding and function of proteins is dependent on the level of available energy within the water in the surrounding tissues. To be biologically active, proteins must acquire a so-called hydration shell consisting of multiple layers of water molecules. Hydration shell water surrounding proteins has physical properties distinct from that of bulk water in the adjacent fluid spaces. When these hydration layers become energy-depleted, protein misfolding is likely to occur. An affordable alternative to pharmaceuticals, which only alter downstream manifestations of the root problem of protein misfolding, is needed.

SUMMARY OF THE INVENTION

According to various forms of the present invention, a system and methods are provided to intentionally manipulate a living protein's hydration layer's energy economy by activating current flow within the body's water compartments via a combination of external, specifically constructed light pulses, which function to alleviate a wide diversity of illnesses, many with devastating personal, social, and economic consequences, while offering an intriguing solution that could be easily implemented at a fraction of the cost of current therapies.

More specifically, the light therapy system and methods of the present invention utilize light emitting diodes to release externally directed, non-coherent light energy in the treatment of animal and plant subjects, including human subjects. This non-coherent light energy is generated by arrays of light emitting diodes at specific, multiple pulsation frequencies (as compared to non-pulsated external light) inducing enhanced energy flow within terrestrial or aquatic animal or plant body water, and ultimately providing for prevention or reversal of disorders related to protein-misfolding in the bodies. In other words, the system and methods of the present invention enhance available cellular energy levels, induce proper protein folding resulting in proper protein function, and promote prevention or reversal of chronic disease, among other benefits. The system and methods of the present invention provide for a non-invasive generation and elevation of energy flow into the subject's body, facilitating intentional excitation of the energetic properties of body water to enhance the dynamics of cells and tissues ability to refold proteins back into their native-fold configurations, thus preventing or reversing protein misfolding diseases.

According to aspects of the present invention, the subject's internal energy economy can be intentionally manipulated by activating current flow within the subject's body water with externally directed light pulses. As a result, a widely diverse array of human illnesses, many with devastating personal, social, and economic consequences, can be amenable to simple modifications in the generation and flow of energy within the body, which offers an intriguing solution that can be easily implemented at a fraction of the cost of current therapies. Likewise, similar economic and intrinsic benefits occur upon the integration of the present invention into plant production systems.

According to one form of the present invention, a light therapy system for treating a subject with light includes an electrical controller configured to control an output of high and low light pulsation frequencies by means of high frequency and low frequency pulse-width-modulators in conjunction with duty cycle controllers, all together providing for the control of light frequencies and light intensities of the system. One or more light sources are electrically connected to and powered by the electrical controller. Each light source includes a plurality of high frequency light emitting elements and a plurality of low frequency light emitting elements to provide a light therapy system which is on (illuminating) for a period of time, followed by a period of time off (non-illuminating), and this on/off cycle repeated a predetermined number of cycles.

According to another form of the present invention, a light therapy system for treating a target or a general area of a subject with non-coherent light includes a light source with a high frequency light emitting element that is powered at high frequency pulsations, and a low frequency light emitting element that is powered at low frequency pulsations. The light therapy system further includes an electrical controller electrically connected to the light source. The electrical controller is configured to power and control the high and low frequency pulsating light emitting elements.

In one aspect, each of the high and low frequency light emitting elements includes a respective plurality of light emitting elements. The plurality of light emitting elements powered at high frequency pulsations are disposed between an array of the plurality of light emitting elements powered at low frequency pulsations.

In another aspect, the electrical controller includes a high frequency pulse-width-modulator and a low frequency pulse-width-modulator. The electrical controller further includes an adjustable high frequency duty cycle controller that controls light pulsation cycles of the high frequency pulse-width modulator, and an adjustable low frequency duty cycle controller that controls light pulsation cycles of the low frequency pulse-width modulator.

In yet another aspect, the electrical controller further includes a first on/off switch operable to activate and deactivate the high frequency pulse-width-modulator and a second on/off switch operable activate and deactivate the low frequency pulse-width-modulator. The electrical controller further includes at least one direct current (DC) power source or at least one alternating current (AC) to DC power converter to directly power the high and low frequency pulse-width-modulators.

In a further aspect, the high frequency light emitting element is configured to be pulsated in a frequency range from 20 kHz to 40 kHz, and the low frequency light emitting element is configured to be pulsated in a frequency range from 500 Hz to 20 kHz.

In a still further aspect, the light therapy system further includes a programmable timer that controls delivery of power to the light therapy system. The timer is configured to control a duration of the light source being illuminated, a duration of the light source not being illuminated, and a predetermined number of cycles of the light source being illuminated and not illuminated.

In yet another aspect, the light therapy system further includes an adjustable mounting assembly to support the light source at a predetermined distance from the target or general area of the subject. The adjustable mounting assembly includes a plurality of height-adjustable legs, vertically extending or telescoping bars with height positioning levers or knobs, and an angle positioning lever for angle positioning of the light source relative to the target or general area of the subject.

In still another aspect, the electrical controller includes a microprocessor-based programmable-memory user-interface. The user-interface includes controls configured to activate pre-programmed or custom sequences, frequencies or intensities of light emitted by the high and low frequency light emitting elements. The user-interface is communicatively connectable to an external computing device or a server for receiving or transmitting data, commands, or software updates. The user-interface also includes a diagnostic mode that performs diagnostic functions of the light therapy system with results displayable on a display screen of the user-interface or transmitted to an external computing device or server for storage and analysis.

According to yet another form of the present invention, a method for treating a target area or a general area of a subject with light therapy includes energizing an electrical controller configured to output high and low frequency voltages, and illuminating a light source with a first and second light emitting elements in response to the energizing of the electrical controller. The illuminating the light source includes modulating the first light emitting element at high frequency pulses and modulating the second light emitting element at low frequency pulses.

In one aspect, the illuminating the light source includes pulsing the first light emitting element in a frequency range from 20 kHz to 40 kHz, and pulsing the second light emitting element in a frequency range from 500 Hz to 20 kHz.

In another aspect, the electrical controller is configured to control predetermined intensities of high and low frequency light.

In yet another aspect, the method includes performing a light therapy cycle by directing high and low frequency light to the target or general area of the subject for a first predetermined duration of time followed by a second predetermined duration of time during which the light source is not illuminated.

In a further aspect, the method includes repeating a plurality of the on/off light therapy cycles a predetermined number of times during a light therapy session.

In a still further aspect, the method includes directing light from the illuminated light source to a volume of drinking water to create pre-conditioned drinking water, and providing the pre-conditioned drinking water to the subject for consumption prior to the performing the light therapy cycle.

In still another aspect, the first light emitting element includes a plurality of high frequency light emitting diodes (LEDs) and the second light emitting element includes a plurality of low frequency LEDs. The plurality of high frequency LEDs are disposed between an array of the plurality of low frequency LEDs.

The present invention is based on the theory that living organisms benefit physiologically from visible light modulated at particular frequencies, especially when subjects are exposed to multiple frequencies of this light at certain intensities for certain durations of exposure. Observed benefits are explainable via the established background of inducing proper protein folding and function. The system of the present invention is simple to use, and relatively inexpensive and portable, thereby enabling greater distribution to those most in need of treatment, and it can reduce or eliminate the need of medication or invasive procedures in animals, enhance health, growth, seed, and/or fruit production in plants, including aquatic plants.

These and other objects, advantages, purposes and features of the present invention will become apparent upon review of the following specification in conjunction with the drawings.

DETAILED DESCRIPTION OF PREFERRED EMBODIMENTS

Figure 1:
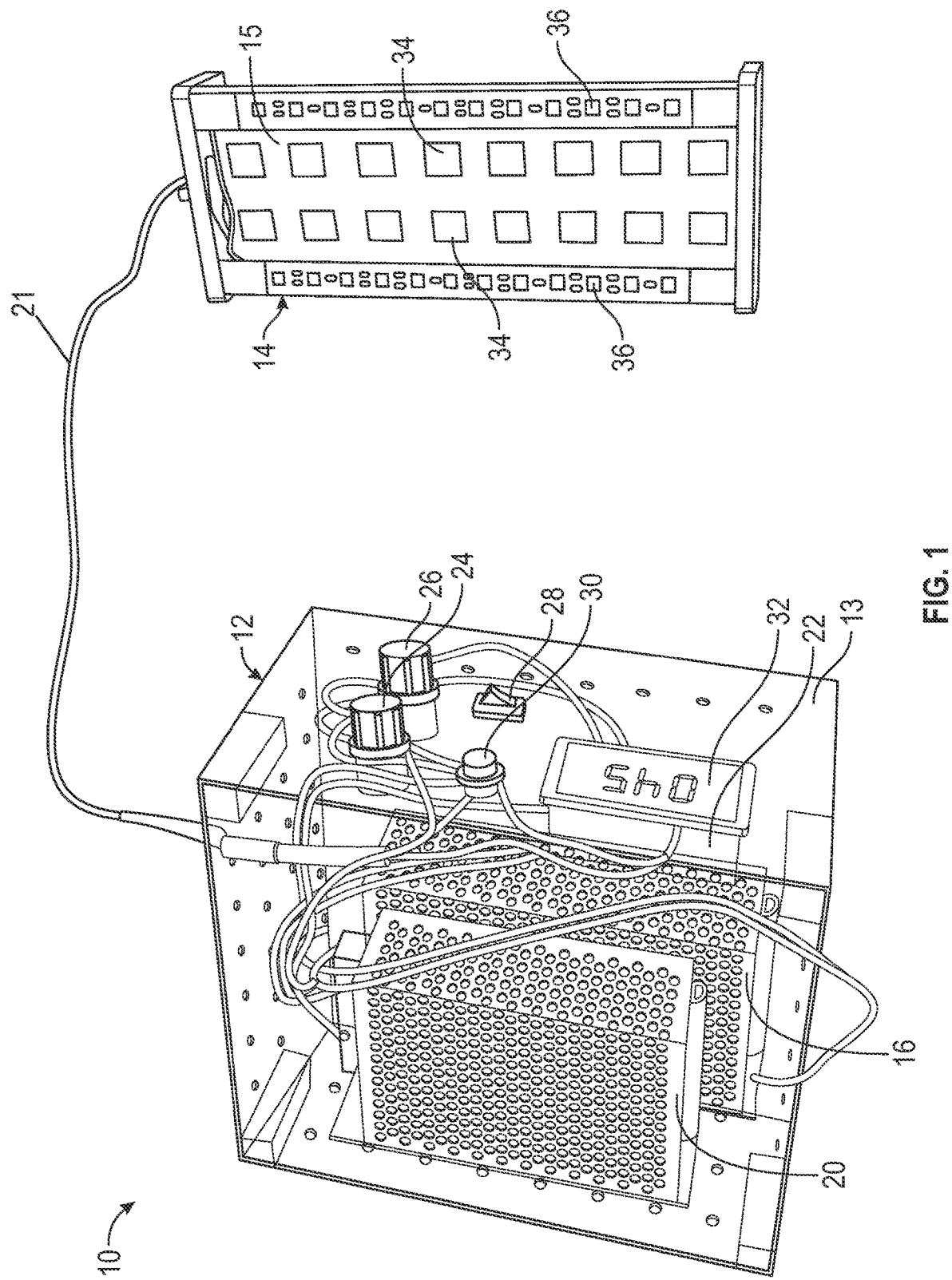
FIG. 1 is a top perspective view of an electrical controller connected to a light source of a light therapy system, in accordance with the present invention.

Referring now to the drawings and the illustrative embodiments depicted therein, as best shown in FIG. 1, a light therapy system 10 includes an electrical controller 12 and a light source 14 electrically connected by a hard-wire to the controller 12. The controller 12 is configured to energize and control output of light emitted through the light source 14. More specifically, the controller 12 is configured to control light modulation frequency, intensity, and duration of the light emitted through the light source 14.

Figure 2A:
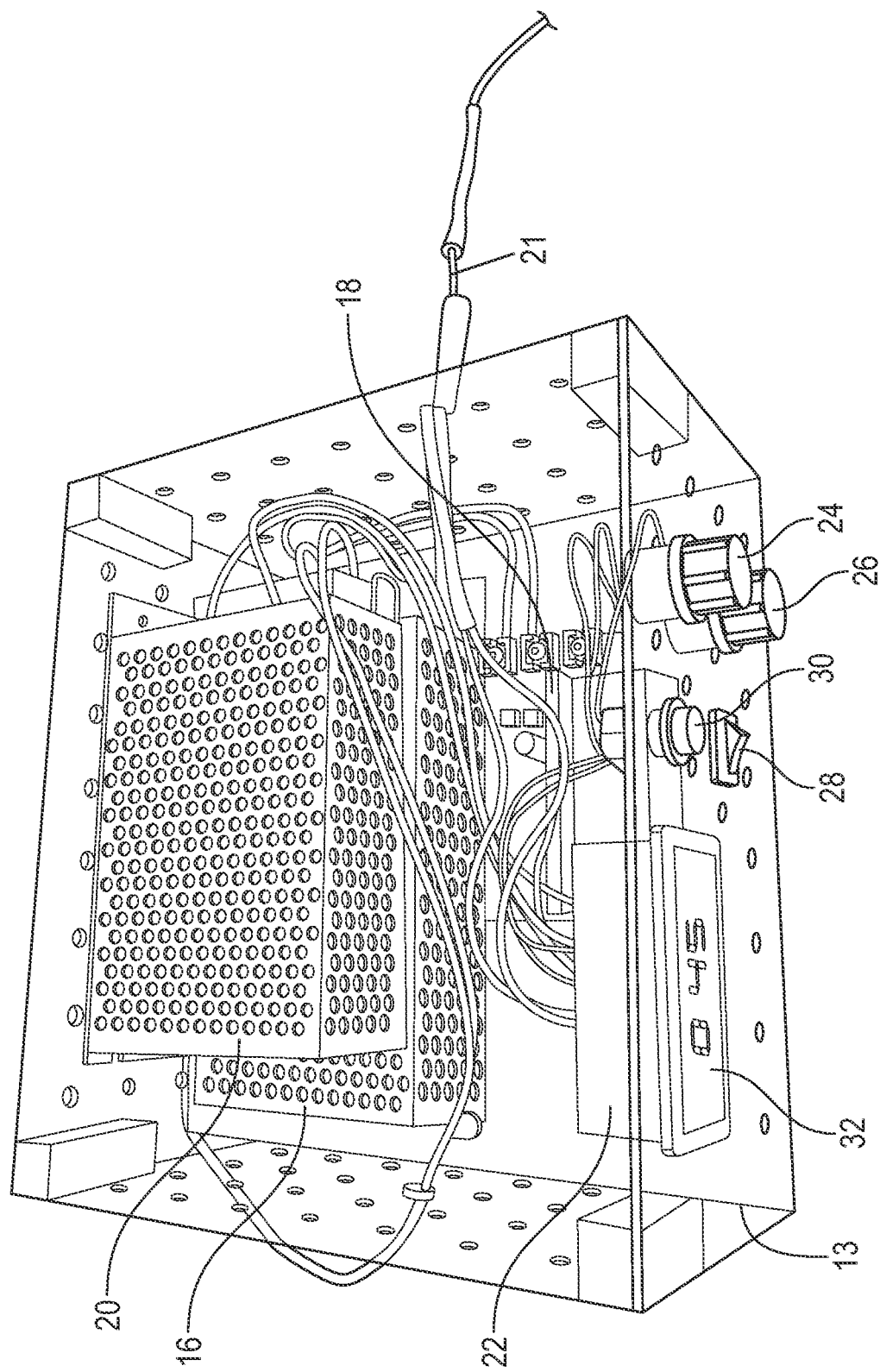
FIG. 2A is a top perspective view of the electrical controller illustrated in FIG. 1.
Figure 2B:
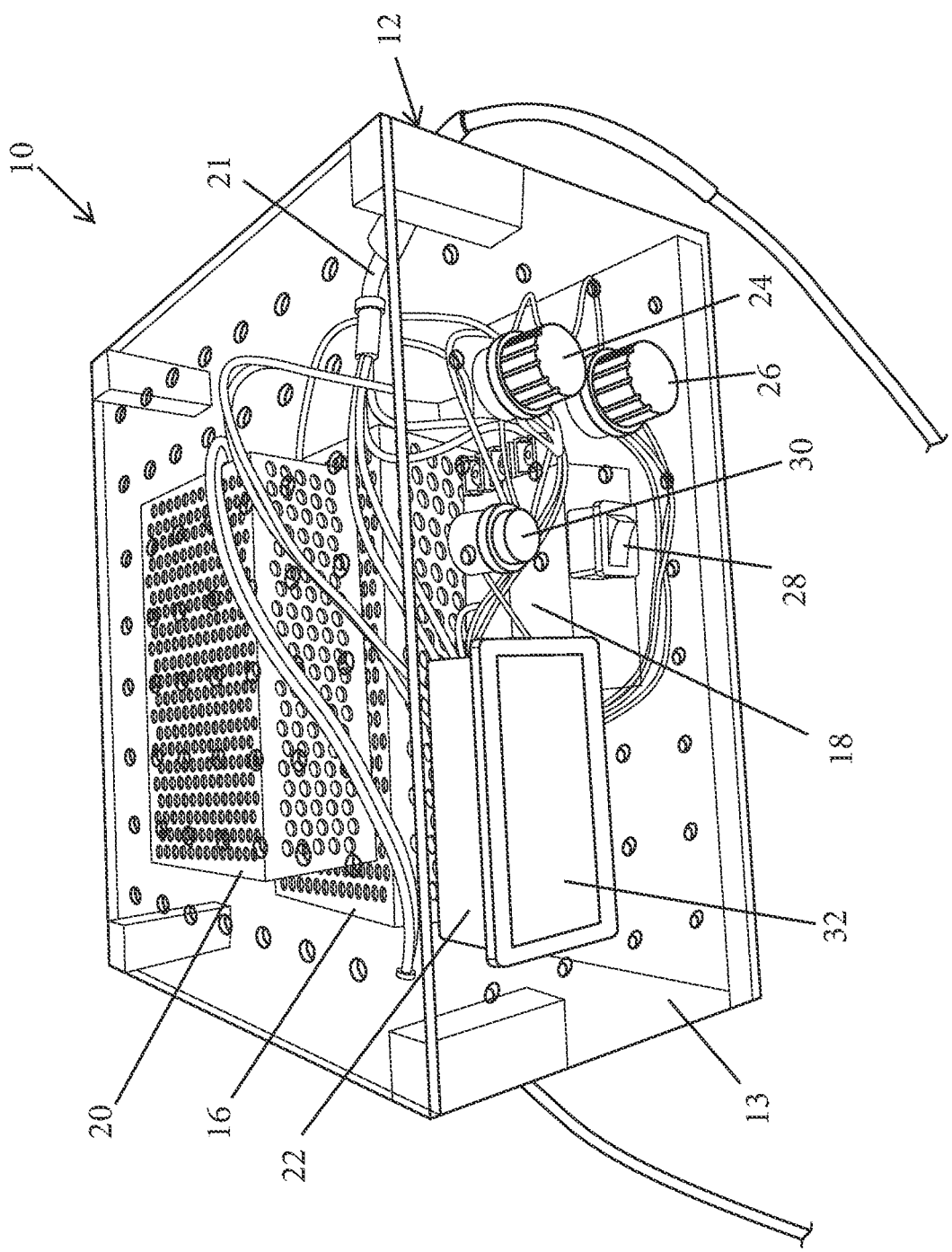
FIG. 2B is a front perspective view of the electrical controller illustrated in FIG. 2A, shown with a top lid attached to the controller.

With reference to FIGS. 1, 2A and 2B, the electrical controller 12 contains a first direct current (DC) switch-mode power supply 16, an electrical output of which may be adjustable, such as from 5 Volt (V) to 48V DC for example. The output of the first DC switch-mode power supply 16 is electrically connected to a high frequency pulse-width-modulator 18, so as to conduct the electrical output of the first DC switch-mode power supply 16 to the high frequency pulse-width-modulator 18. The controller 12 also contains a second DC switch-mode power supply 20, an electrical output of which may be adjustable, such as from 5V to 48V DC for example. The second DC switch-mode power supply 20 is electrically connected to a low frequency pulse-width-modulator 22, so as to conduct the electrical output of the second DC switch-mode power supply 20 to the low frequency pulse-width-modulator 22. The high frequency pulse-width-modulator 18 is configured to output electrical voltage switching from 0-100% of the DC voltage supplied by the first power supply 16 at a higher frequency range, such as between 20 kHz to 40 kHz, while the low frequency pulse-width-modulator 22 is configured to output electrical voltage switching from 0-100% of the DC voltage supplied by the second power supply 20 at a lower frequency range, such as between 500 Hz to 20 kHz. Although the first and second power supplies 16, 20 are shown in a stacked arrangement and the high and low frequency pulse-width-modulators 18, 22 are shown separate from one another, it will be appreciated that it is possible to alternate positioning and/or arrangements of the power supplies 16, 20 relative one another, and of the high and low frequency pulse-width-modulators 18, 22 relative one another. In the illustrated embodiment, the controller 12 may be powered by a typical 120V alternating current (AC) source. However, it is also envisioned that the controller 12 may be powered by other AC voltage sources, or an alternate DC voltage source, such as a DC to DC power converter, or a rechargeable onboard battery.

An exterior side 13 of the controller 12 includes an adjustable high frequency duty cycle controller 26 electrically connected to the high frequency pulse-width-modulator 18, and an adjustable low frequency duty cycle controller 24 electrically connected to the low frequency pulse-width-modulator 22. It should be understood that the adjustable high and low frequency duty cycle controllers 26 and 24 may be provided as knobs, switches, sliders and the like, so long as they are capable of providing control and adjustability of duty cycles of the pulse-width-modulators 18 and 22 anywhere from 0-100% of the respective electrical voltage outputs. The exterior side 13 further includes a high frequency on/off switch 28 and a low frequency on/off switch 30 that are electrically connected to and operable to turn on and off the high frequency pulse-width-modulator 18 and the low frequency pulse-width-modulator 22, respectively. It should be appreciated that the switches 28 and 30 may be push buttons, toggle switches, or the like, so long as they enable a user to turn on or off the source of electrical power to light source 14.

Optionally, the electrical controller 12 may be plugged into a commercially available programmable wall timer (not shown) that is programmed to control the source of electrical AC power to the electrical controller 12 for specific durations of time on, specific durations of time off, and a predetermined number of repeated on/off cycles thereof during a light therapy session. The functions of such a timer may be incorporated into light therapy system 10 and electrically connected to the controller 12. The programmable timer may alternatively be integrated into the electrical controller 12.

As seen in FIGS. 1, 2A and 2B, in the illustrated embodiment the exterior side 13 has a digital display screen 32 that is incorporated and electrically connected with the low frequency pulse-width-modulator 22. The digital display 32 is configured to provide digital representation of the duty cycle output of the low frequency pulse-width-modulator 22. Optionally, the exterior side 13 may also include a digital display screen (not shown) electrically connected to the high frequency pulse-width-modulator 18 and configured to provide digital representation of the duty cycle output of the high frequency pulse-width-modulator 18.

Figure 4A:
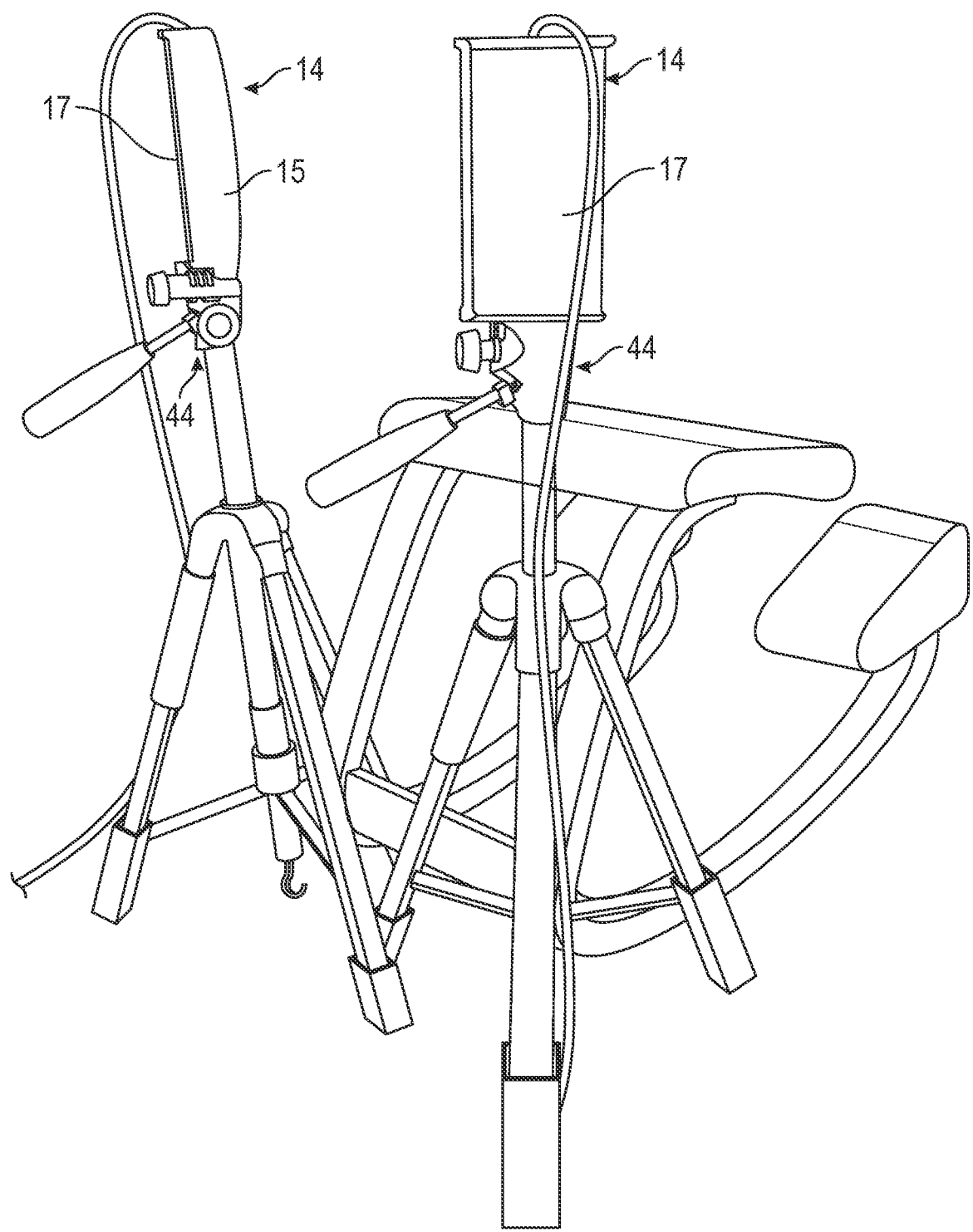
FIG. 4A is a rear and side perspective view of two respective light sources emitting light therapy.

In the illustrated embodiment, and as best shown in FIGS. 1 and 4A, the light source 14 is generally a rigid rectangular block with a front side 15 and a back side 17. With reference to FIG. 1, the front side 15 includes a plurality of high frequency powered light emitting diode (LED) chips 34 electrically connected with one another and powered by high frequency pulse-width-modulator 18, and a plurality of low frequency powered LED chips 36 electrically connected with one another and powered by low frequency pulse-width-modulator 22 and disposed along opposite sides of the high frequency powered LED chips 34. Although the plurality of high frequency powered LED chips 34 are shown in FIG. 1 as two parallel, adjacent, and longitudinally extending rows of LED chips, other configurations and arrangements of the high frequency powered LED chips 34 are envisioned. Similarly, although the plurality of low frequency powered LED chips 36 are shown as two parallel and longitudinally extending rows of LED chips disposed along each respective longitudinal side of the light source 14, other configurations and arrangements of the low frequency powered LED chips 36 are envisioned. In the illustrated embodiment, the light source 14 includes from twelve to eighteen of the low frequency powered LED chips 36 on each side and from four to fifty-six of the high frequency powered LED chips 34 in between. It should also be appreciated that the light source 14 may have a different shape, such as a square, circle, or the like. The back side 17 may be made of wood, plastic, or other non-magnetic or non-magnetically permeable materials.

Generally, the high and low frequency powered LED chips 34, 36 of the light source 14 are electrically connected by a hard-wire 21 to the respective high and low frequency pulse-width-modulators 18 and 22, such that the light source 14 is capable of producing light at a specified modulation frequency and intensity for the desired duration of time with the high frequency powered LED chips 34 producing light at a "higher" frequency between 20 kHz to 40 kHz, and the low frequency powered LED chips 36 producing light at a "lower" frequency between 500 Hz to 20 kHz. The light produced by the light source 14 is of a variable intensity, which is achieved by adjusting duty cycle controllers 26 and 24. A "duty cycle" is the ratio, commonly expressed as a percentage of time during which a load, voltage, or circuit remains on or active compared to the time the load, voltage, or circuit is off or inactive. For example, a 60% duty cycle is a signal that is ON 60% of the time and OFF the other 40% of the time.

Figure 3A:
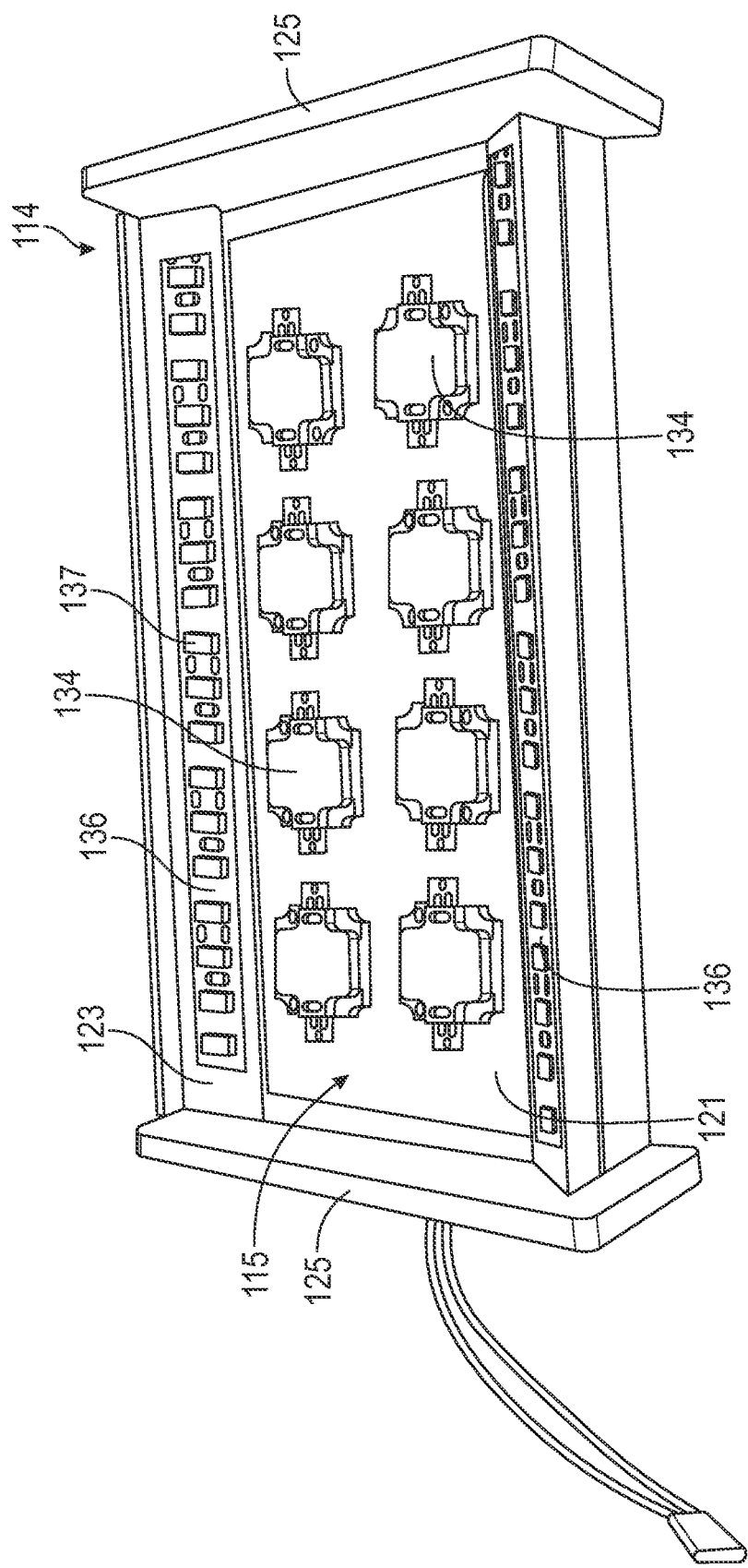
FIG. 3A is a front perspective view of a light source for use in connection with the electrical controller for body treatments.
Figure 3B:
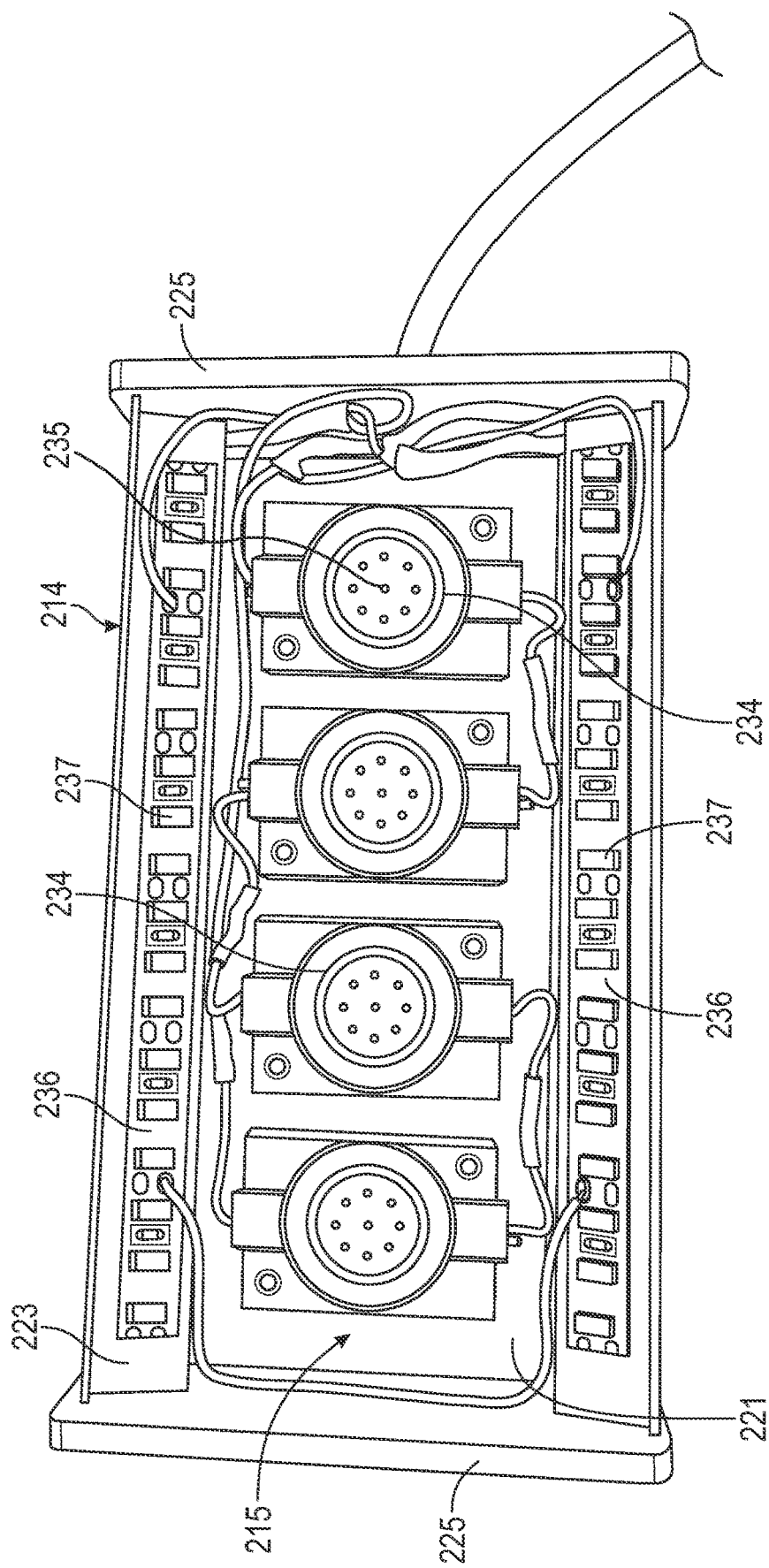
FIG. 3B is a front perspective view of a light source for use in connection with the electrical controller for neuro treatments.

FIGS. 3A and 3B illustrate alternative embodiments of light sources, one of which is a "body light" 114 (FIG. 3A) and the other of which is a "neuro-light" (FIG. 3B). The body light 114 is intended to administer a relatively more intense light therapy, typically (but not exclusively) to the body core and/or appendages. The neuro light is intended to administer light therapy at a relatively lower intensity, typically (but not exclusively) to the face and eyes. It will be appreciated that the light source 14 and/or the alternative light source devices 114, 214 described in more detail below may be utilized with the light therapy system 10 in a light therapy session. It will be understood that components of the alternative light source devices of FIGS. 3A and 3B, which correspond to components of the light source 14, are assigned corresponding numerals with the addition of 100 and 200, respectively.

With reference to FIG. 3A, the body light source device 114 is designed for use in connection with the electrical controller 12 to treat target body-related disorders. The light source 114 is a generally rectangular block with a front side 115 and a back side (not shown). The front side 115 includes a plurality of high frequency powered square "cob" modules 134, each packed with nine 12V LEDs. Each cob module 134 is electrically connected with one another and powered by high frequency pulse-width-modulator 18. In the illustrated embodiment of FIG. 3A, there are a total of eight high frequency powered square cob modules 134, arranged as two parallel rows of four square cob modules in each row. However, other quantities and arrangements of the high frequency powered square cob modules 134 are also possible. The high frequency powered square cob modules 134 are configured to emit light in a light focusing manner, which is preferred for light therapy of target body-related disorders. The LEDs used in the square cob modules 134 are high-speed switching LEDs with color range "cool white", i.e. having color temperature of at least 4,000 Kelvin (K) or higher. However, other light color ranges of the high-speed switching LEDs are also possible.

The front side 115 further includes a plurality of low frequency powered LED strips 136. Each LED strip 136 includes a plurality of 12V LED chips 137 electrically connected with one another. The LED strips 136 are electrically connected with one another and powered by low frequency pulse-width-modulator 22. In the illustrated embodiment of FIG. 3A, there are two low frequency powered LED strips 136, with each LED strip including eighteen 12V LED chips 137. The two low frequency powered LED strips 136 are disposed along respective opposing sides of the front side 115, with the rows of the high frequency powered square cob modules 134 positioned in between the two low frequency powered LED strips 136. The LED chips 137 used in the strips 136 are high-speed switching LEDs with color range having color temperature of at least 4,000 K or higher. However, other light color ranges of the high-speed switching LEDs are also possible.

In the illustrated embodiment of FIG. 3A, front side 115 further includes a wide plate 121 for supporting the plurality of high frequency powered square cob modules 134 and a pair of narrow plates 123 for supporting respective low frequency powered LED strips 136. It is contemplated that the wide plate 121 and the narrow plates 123 are made of aluminum to help dissipate heat energy away from the LEDs. It is further envisioned that the wide plate 121 is generally co-planar with the front side 115, while the narrow plates 123 are angled relative to the wide plate 121, such that in cooperation with transverse plates 125 of the light source 114 a trough-like or cradle-like front side surface is formed.

Referring now to FIG. 3B, the neuro light source 214 is designed for use in connection with the electrical controller 12 to treat general neuro-related disorders. The light source 214 is a generally rectangular block with a front side 215 and a back side (not shown). The front side 215 includes a plurality of high frequency powered round cob modules 234, each packed with nine 12V LEDs 235. In the illustrated embodiment of FIG. 3B, there are a total of four high frequency powered round cob modules 234 arranged in a single row, with each cob module 234 being electrically connected with one another and powered by high frequency pulse-width-modulator 18. However, other quantities and arrangements of the high frequency powered round cob modules 234 are also possible. The round cob modules 234 are configured to emit light in a light diffusing manner, which is preferred for light therapy of general neuro-related disorders. The LEDs used in the high frequency powered round cob modules 234 are high-speed switching LEDs with color range having color temperature of at least 4,000 K or higher. However, other light color ranges of the high-speed switching LEDs are also possible.

The front side 215 further includes a plurality of low frequency powered LED strips 236. Each LED strip 236 includes a plurality of 12V LED chips 237 electrically connected with one another. The strips 236 are electrically connected with one another and powered by low frequency pulse-width-modulator 22. In the illustrated embodiment of FIG. 3B, there are two low frequency powered LED strips 236 with each LED strip including eighteen 12V LED chips 237. The two low frequency powered LED strips 236 are disposed along respective opposing sides of the front side 215, with a single row of the high frequency powered round cob modules 234 positioned in between the two low frequency powered LED strips 236. The LEDs used in the strips 236 are high-speed switching LEDs with color range having color temperature of at least 4,000 K or higher. However, other light color ranges of the high-speed switching LEDs are also possible.

The front side 215 further includes a wide plate 221 for supporting the plurality of high frequency powered round cob modules 234 and a pair of narrow plates 223 for supporting respective low frequency powered LED strips 236. It is contemplated that the wide plate 221 and the narrow plates 223 are made of aluminum to help dissipate heat energy away from the LEDs. It is further envisioned that the wide plate 221 is generally co-planar with the front side 215, while the narrow plates 223 are angled relative to the wide plate 221, such that in cooperation with transverse plates 225 of the light source 214 a trough-like or cradle-like front side surface is formed.

Figure 4B:
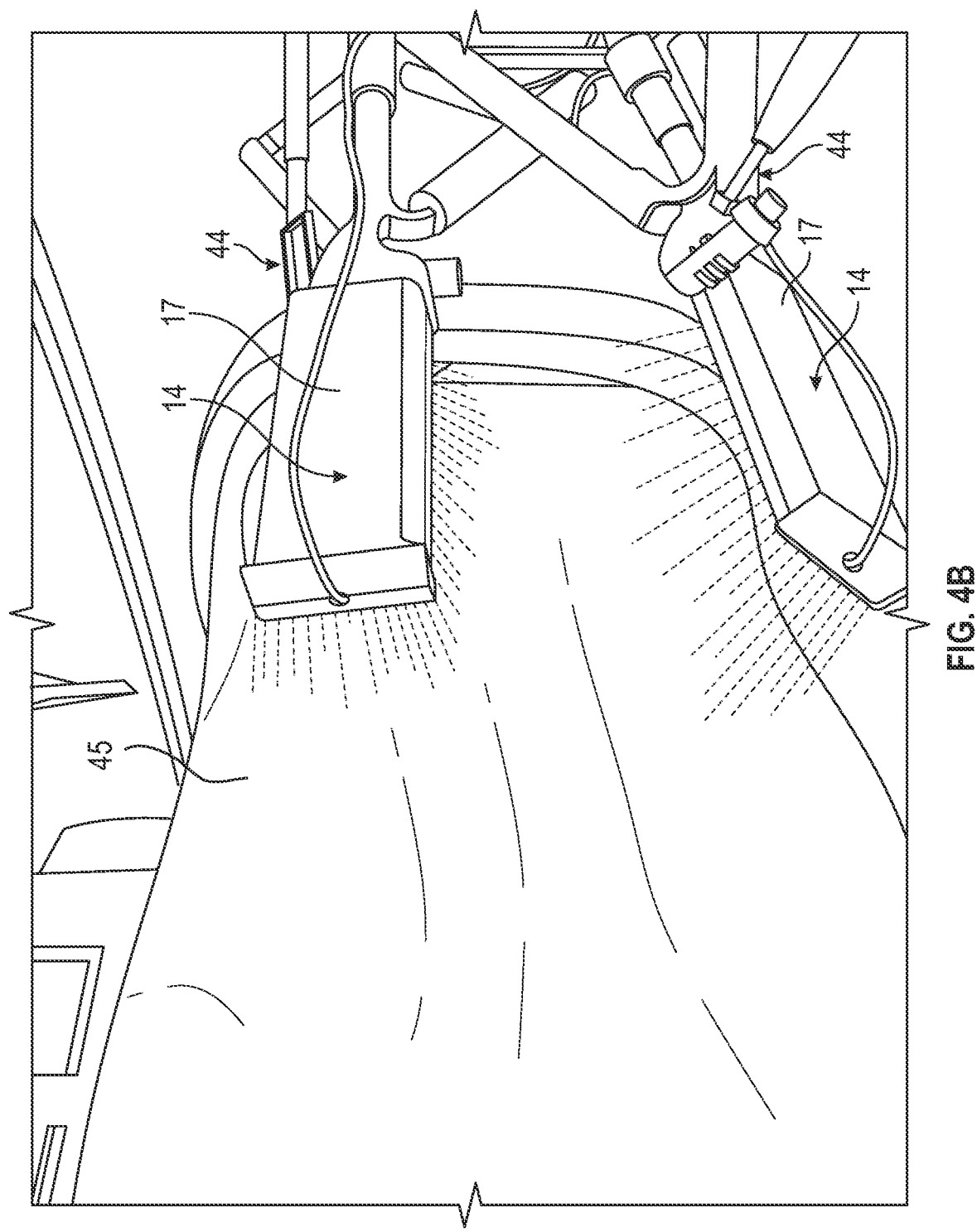
FIG. 4B is a top perspective view of the two light sources of FIG. 4A, shown emitting light therapy to target areas of a subject.

The light therapy system may further include mounts or tripods 44 for mounting, positioning and/or supporting the light source(s) 14, 114 or 214 close to a target area of the subject's body requiring treatment, such as shown in FIGS. 4A and 4B. For example, in the illustrated embodiment of FIG. 4B a pair of tripods 44 are shown, with each tripod 44 supporting one light source 14 positioned to emit light onto the kidney areas of the subject's body 45. The mount 44 may include a plurality of height-adjustable legs, vertically extending or telescoping bar with a height positioning lever or knob, and/or an angle positioning lever to facilitate setting a desired orientation of the light source 14, 114 or 214 relative to the target area of the subject's body.

Figure 5:
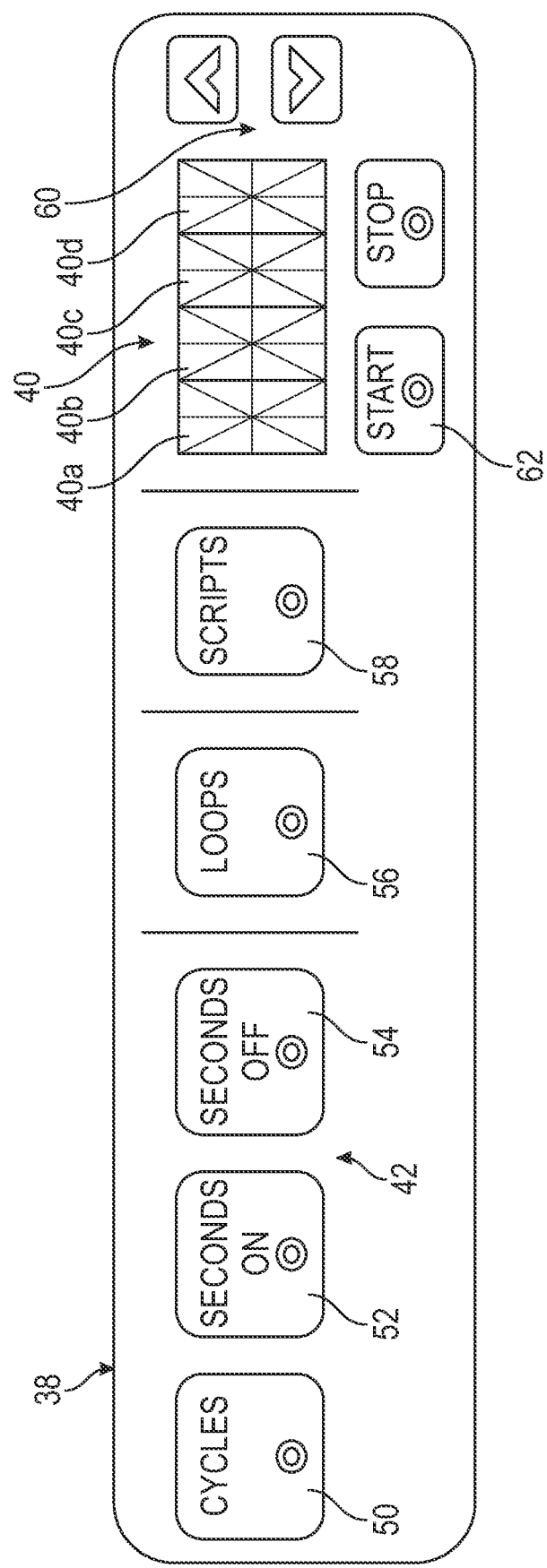
FIG. 5 is a schematic view of one example of a user interface of the light therapy system.

It is further contemplated within the scope of the present invention that a user interface (UI) 38, one example thereof schematically shown in FIG. 5, may be integrated with the controller 12. The user interface 38, as described in more detail below, is equipped and configured to replace high and low frequency duty cycles 26, 24, high and low frequency on/off switches 28, 30, and the digital display screen 32, as well as to add enhanced control features. It will be appreciated, however, that user interface 38 may optionally be integrated with or externally connected to the controller 12 without replacing or eliminating the manual controllers immediately described above from the front face 13 of the controller 12.

With reference to FIG. 5, user interface 38 may provide pre-programmed controls for executing pre-set sequences of light modulated frequencies, duty cycles, on/off durations, and number of repeated on/off cycles, as well as user-programmed custom control of light therapy parameters for treatment in reversal or prevention of a number of disorders in connection with various parts of a subject's body. In the illustrated embodiment, the user interface 38 includes a display screen 40 and controls 42 for custom or pre-set adjustments to the light sequences provided to the subject. The user interface 38 may also include a processor and memory to store computer-readable instructions for programmed operation of the system 10. Optionally, the user interface 38 may further be connectable, wirelessly or by hard-wire, to an external computing device or a server to receive and/or transmit data, commands and/or software updates. And it is further envisioned that the user interface 38 may be configured in a diagnostic mode to perform diagnostic functions of the light therapy system 10, results of which may be displayed on the display screen 40 of the user interface 38, or transmitted to the external computing device or server for storage and analysis.

In the illustrated embodiment of FIG. 5, the controls 42 of the user interface 38 include a cycles control button 50 that initiates a "cycle" defined as a single on/off sequence having specified "seconds on" and "seconds off", for which respective "seconds on" control button 52 and seconds off control button 54 are provided. The user interface 38 further includes a loops control button 56, and a scripts control button 58. In the description that follows, a "loop" is defined as a number of repetitions of a given cycle, and a "script" is defined as sequences of loops. An exemplary method of operating the user interface 38 is described in more detail below.

To select a desired duty cycle, press the "cycles" control button 50, after which the cycles LED illuminates steadily, with a first or far-left digit 40*a* of the display 40 indicating the cycle number, e.g. "1" for cycle #1, etc. Continue pressing the "cycles" control button 50 to advance through the cycle numbers, with "9" being the maximum number of cycles allowed, followed by "1". Cycle #1, controlled by a micro-controller (not shown) of the light therapy system 10, is originally a factory-default cycle consisting of 240 seconds on, 120 seconds off. The factory-default cycle #1 may later be re-programmed by an operator to become operator-defined, at which time cycle #1 may be over-written to provide up to nine operator-defined cycles. While displaying a cycle number in the first digit 40*a* of the display 40, press the "seconds on" control button 52 (its LED is lit steady) to display the seconds on for that given cycle in the latter or right three digits 40*b-d* (i.e. second, third, and fourth digits) of the display 40. Similarly, press the "seconds off" control button 54 to display the seconds off for that given cycle. For example, factory-default cycle #1 would steady display "1240" for when the "seconds on" control button 52 is pressed, and "1120" for when the "seconds off" control button 54 is pressed.

Cycle numbers 2-9 are operator-defined. If a cycle has never been operator-defined, the display 40 will show the cycle number steady in first digit 40*a* followed by "---" in the latter digits 40*b-d* blinking at 1 Hz, thereby indicating such. To initially program an operator-defined cycle press and hold the "seconds on" control button 52 for three seconds (its LED begins blinking at 1 Hz) and enter desired "on" seconds (maximum 999 seconds) using the up/down arrows 60 (displayed seconds will blink at 1 Hz until confirmed). Then press the "seconds on" control button 52 to confirm (its LED and displayed numbers cease blinking). After approximately one second, UI automatically jumps to the seconds off (its LED will begin blinking at 1 Hz), at which point same programming format may be repeated for the seconds off, at which time the display and all LEDs are blanked except for the cycle number being steady on, and the cycles LED being steady on indicating that the cycle has been defined. To re-program an operator-defined cycle, while a cycle number is showing steady in the first digit 40*a* of the display 40, press and hold the "seconds on" control button 52 for three seconds to enter into programming mode, the seconds on LED and the latter digits 40*b-d* of the display 40 begin blinking, at which point the programming pattern described above can be followed.

By pressing the "loops" control button 56, the loops LED illuminates steadily, with the first digit 40*a* of the display 40 indicating the loop number, e.g. "1" for loop #1, etc. Continue pressing the "loops" control button 56 to advance through the loop numbers, with "9" being the maximum number of loops allowed, followed by "1". Loop #1 is a fixed factory-default loop consisting of 7 loops of factory-default cycle #1, i.e. fixed until over-written by an operator to become operator-defined. While displaying a loop number in the first digit 40*a* of the display 40, its related cycle number will appear immediately to the right in second digit 40*b*, followed by number of loops defined of that cycle in third digit 40*c* and fourth digit 40*d*, e.g. loop #1 factory-default would steady display "1107". Loop numbers 2-9 are operator-defined. If a loop has never been operator-defined, the display will show the loop number steady in first digit 40*a* followed by "---" in latter digits 40*b-d* blinking at 1 Hz, thereby indicating such.

To initially program an operator-defined loop, press and hold the "loops" control button 56 for three seconds (its LED begins blinking at 1 Hz). Then press the "cycles" control button 50 until the desired cycle number is displayed in second digit 40*b* of the display 40. After that, enter the desired number of loops of that cycle in the flashing third and fourth digits 40*c-d* using the up/down arrows 60 (maximum number of loops/cycle being 99), with the displayed loops blinking at 1 Hz until confirmed. Press the "loops" control button 56 again to confirm, at which time all blinking stops with display 40 showing four digits steady and the loops LED lit steady indicating the loop has been defined. To re-program an operator-defined loop, while a loop number is showing steady in first digit 40*a* of the display 40, press and hold the "loops" control button 56 for three seconds to enter into programming mode, the loops LED and the latter digits 40*b-d* in the display begin blinking, at which point the programming pattern described above can be followed.

To select a script sequence, press the "scripts" control button 58, at which point the scripts LED illuminates steadily, with the first digit 40a of the display 40 indicating the script number, e.g. "1" for script #1, etc. Continue pressing the "scripts" control button 58 to advance through the script numbers, with "9" being the maximum number of scripts allowed, followed by "1". Script #1 is a fixed factory-default script consisting of factory-default loop #1 only, i.e. fixed until over-written by an operator to become operator-defined. While displaying a script number in the first digit 40a of the display 40, its related loop(s) will appear immediately to the right in the latter digits 40b-d, e.g. script #1 being factory-default of loop #1 would only steadily display "11--".

Scripts 2-9 are operator-defined. If a script has never been operator-defined, the display will show the script number steady in first digit 40a followed by "---" in the latter digits 40b-d blinking at 1 Hz, thereby indicating such. To initially program an operator-defined script, press and hold the "scripts" control button 58 for three seconds (its LED begins blinking at 1 Hz), then use the up/down arrows 60 until the first desired loop number in the second digit 40b of the display 40 appears. After that, press the "loops" control button 56 to confirm the first loop desired. If a second loop is desired in the script, press the "scripts" control button 58 again and use the up/down arrows 60 to select a second loop in the third digit 40c of the display 40, after which press the "loops" control button 56 to confirm the second loop in the script. If a third loop is desired in the script, press the "scripts" control button 58 again and use the up/down arrows 60 to select a third loop in the fourth digit 40d of the display 40, after which press the loops control button 56 to confirm the third loop in the script. To finish programming the script at any time, press and hold the "scripts" control button 58 for three seconds. To re-program an operator-defined script, while a script number and the related loops are showing steady in the first digit 40a of the display, press and hold the "scripts" control button 58 for three seconds to enter into programming mode, the scripts LED and the latter digits 40b-d of the display begin blinking, at which point the programming pattern described above can be followed.

It is further contemplated that user interface ("UI") pads would have medium tactile feel, and, except press & hold functions, become active upon user's release of the tactile pad. All blinking indicators will cease after ten seconds of no UI activity and the unit will revert to last confirmed programming and unit will be in ready-mode. Pressing and holding the down arrow and stop button simultaneously for five seconds will clear all programming and reset the unit back to factory defaults. Pressing and holding the up arrow and the start button simultaneously for five seconds will put the unit in a constant-on mode, repeat press & hold to exit the constant-on mode. Pressing and holding the cycles and scripts buttons simultaneously for five seconds will put the unit in a child-lock mode; repeat press & hold to exit the child-lock mode. Pressing and holding the "seconds on" and "seconds off" simultaneously for five seconds will put the unit in a duty-cycle adjustment mode for the 24V pulse-width-modulator. Use up & down arrows to adjust duty cycle from 35% to 65% in 5% increments, repeat press & hold to exit the duty-cycle adjustment mode. Pressing and holding the loops and scripts control buttons simultaneously for five seconds will put the unit in a duty-cycle adjustment mode for the 48V pulse-width-modulator. Use up & down arrows to adjust duty cycle from 35% to 65% in 5% increments, and repeat press & hold to exit the duty-cycle adjustment mode. By pressing & holding the "start" button 62 for three seconds the unit is allowed 1-minute delayed start. All LEDs and LED indicators are cool white color.

In one example of a therapeutic use of the light therapy system 10, it is contemplated that over a variable trial period the subject should receive daily light therapy delivered in pulsed fashion with a 4-minute period of light exposure from the light source 14 followed by a 2-minute interval during which no light is emitted by the light source 14. This on/off cyclical pattern may be repeated 7 times so that treatment duration is approximately 40 minutes. According to one illustrative method, light is administered from right and left sides of the target area, at least eight inches from the skin or plant surface, at about a 45° angle with respect to the subject's coronal plane. The subject may receive one to two such treatments per day, for example.

Although one light source 14, 114 or 214 of the light therapy system 10 may be used during a light therapy treatment, preferably two light sources 14, 114, 214, or a combination thereof, positioned opposite one another, may also be used during the treatment, such as shown in FIGS. 4A and 4B. It will thus be appreciated that a plurality of light sources 14, 114, and/or 214 may be utilized to further increase the effect of the treatment, and if so employed, the plurality of light sources 14, 114, and/or 214 may be electrically connected to one electrical controller 12, or to a plurality of separate electrical controllers 12. Optionally, it is envisioned that drinking water may be treated by the light therapy system 10 to create pre-conditioned drinking water, and the pre-conditioned drinking water then provided to the subject for ingestion prior to a light therapy session. Consumption of pre-conditioned (light-treated) drinking water by the subject prior to a light therapy session may enhance the effectiveness of the session by introducing the pre-conditioned water to the subject's interstitial tissues.

The preferred embodiments described herein thus provide for a light therapy system and methods of an external light source oscillating at distinct frequencies, to deliver acceleration of reversal and/or a decrease in susceptibility to certain protein misfolding illnesses of target and/or general areas of a human, animal or plant bodies.

Changes and modifications in the specifically described embodiments may be carried out without departing from the principles of the present invention, which is intended to be limited only by the scope of the appended claims, as interpreted according to the principles of patent law including the doctrine of equivalents.

The embodiments of the invention in which an exclusive property or privilege is claimed are defined as follows:

1. A light therapy system for treating a target or a general area of a subject with non-coherent light, said system comprising:
   a light source comprising a high frequency light emitting element configured to be powered at high frequency pulsations in a frequency range from 20 kHz to 40 kHz, and a low frequency light emitting element configured to be powered at low frequency pulsations in a frequency range from 500 Hz to 20 kHz; and
   an electrical controller electrically connected to said light source;
   wherein said electrical controller is configured to power and control said high and low frequency pulsating light emitting elements.

2. The light therapy system of claim 1, wherein each of said high frequency light emitting element and said low frequency light emitting element comprises a respective plurality of light emitting elements.

3. The light therapy system of claim 2, wherein said plurality of light emitting elements powered at high frequency pulsations are disposed between an array of said plurality of light emitting elements powered at low frequency pulsations.

4. The light therapy system of claim 1, wherein said electrical controller comprises a high frequency pulse-width-modulator and a low frequency pulse-width-modulator.

5. The light therapy system of claim 4, wherein said electrical controller further comprises an adjustable high frequency duty cycle controller configured to control light pulsation cycles of said high frequency pulse-width modulator, and an adjustable low frequency duty cycle controller configured to control light pulsation cycles of said low frequency pulse-width modulator.

6. The light therapy system of claim 4, wherein said electrical controller further comprises a first on/off switch operable to activate and deactivate said high frequency pulse-width-modulator and a second on/off switch operable activate and deactivate said low frequency pulse-width-modulator.

7. The light therapy system of claim 4, wherein said electrical controller comprises at least one direct current (DC) power source or at least one alternating current (AC) to DC power converter to directly power said high and low frequency pulse-width-modulators.

8. The light therapy system of claim 1, further comprising a programmable timer configured to control delivery of power to said light therapy system, wherein said timer is configured to control a duration of said light source being illuminated, a duration of said light source not being illuminated, and a predetermined number of cycles of said light source being illuminated and not illuminated.

9. The light therapy system of claim 1, further comprising an adjustable mounting assembly to support said light source at a predetermined distance from the target or general area of the subject, said adjustable mounting assembly comprising a plurality of height-adjustable legs, vertically extending or telescoping bars with height positioning levers or knobs, and an angle positioning lever for angle positioning of said light source relative to the target or general area of the subject.

10. The light therapy system of claim 1, wherein said electrical controller comprises a microprocessor-based programmable-memory user-interface, wherein said user-interface comprises controls configured to activate pre-programmed or custom sequences, frequencies or intensities of light emitted by said high and low frequency light emitting elements.

11. The light therapy system of claim 10, wherein said user-interface is communicatively connectable to an external computing device or a server for receiving or transmitting data, commands, or software updates.

12. The light therapy system of claim 10, wherein said user-interface comprises a diagnostic mode that is configured to perform diagnostic functions of said light therapy system with results displayable on a display screen of said user-interface or transmitted to an external computing device or server for storage and analysis.

13. A method for treating a target area or a general area of a subject with light therapy, said method comprising:
    energizing an electrical controller configured to output high and low frequency voltages; and
    illuminating a light source in response to said energizing the electrical controller, wherein the light source comprises a first and second light emitting elements;
    wherein said illuminating the light source comprises modulating the first light emitting element at high frequency pulses in a frequency range from 20 kHz to 40 kHz, and modulating the second light emitting element at low frequency pulses in a frequency range from 500 Hz to 20 kHz.

14. The method of claim 13, wherein the electrical controller is configured to control predetermined intensities of high and low frequency light.

15. The method of claim 13, further comprising performing a light therapy cycle by directing high and low frequency light to the target or general area of the subject for a first predetermined duration of time followed by a second predetermined duration of time during which the light source is not illuminated.

16. The method of claim 15, comprising repeating a plurality of the on/off light therapy cycles a predetermined number of times during a light therapy session.

17. The method of claim 15, further comprising directing light from the illuminated light source to a volume of drinking water to create pre-conditioned drinking water, and providing the pre-conditioned drinking water to the subject for consumption prior to said performing the light therapy cycle.

18. The method of claim 13, wherein the first light emitting element comprises a plurality of high frequency light emitting diodes (LEDs) and the second light emitting element comprises a plurality of low frequency LEDs, and wherein the plurality of high frequency LEDs are disposed between an array of the plurality of low frequency LEDs.

19. A light therapy system for treating a target or a general area of a subject with non-coherent light, said system comprising:
    a light source comprising a plurality of first light emitting elements configured to output high frequency light pulsations and a plurality of second light emitting elements configured to output low frequency light pulsations, wherein said first light emitting elements are pulsated in a frequency range from 20 kHz to 40 kHz and said second light emitting elements are pulsated in a frequency range from 500 Hz to 20 kHz, and wherein said first light emitting elements are disposed between an array of said second light emitting elements; and
    an electrical controller electrically connected to said light source, wherein said electrical controller is configured to power and control said first and second light emitting elements, and said electrical controller comprises:
        a high frequency pulse-width-modulator and a low frequency pulse-width-modulator;
        an adjustable high frequency duty cycle controller configured to control light pulsation cycles of said high frequency pulse-width modulator and an adjustable low frequency duty cycle controller configured to control light pulsation cycles of said low frequency pulse-width modulator;
        an on/off switch operable to activate or deactivate said high frequency pulse-width-modulator and an on/off switch operable to activate and deactivate said low frequency pulse-width-modulator;
        a programmable user interface with a processor and memory, said programmable user interface comprising a plurality of controls configured to activate pre-programmed or custom sequences, frequencies and intensities of light emitted by said first and second light emitting elements; and at least one direct current (DC) power source and at least one alternating current (AC) to DC power converter to directly power said high and low frequency pulse-width-modulators; and a programmable timer configured to control delivery of power to said electrical controller to thereby control a duration of said light source being illuminated, a duration of said light source not being illuminated, and a predetermined number of cycles of said light source being illuminated and not illuminated.

\* \* \* \* \*